US005938652A

United States Patent [19]
Sauer

[11] Patent Number: 5,938,652
[45] Date of Patent: Aug. 17, 1999

[54] ABSORBENT ARTICLE HAVING A SELECTIVELY ELASTICIZED WAIST FLAP

[75] Inventor: Barbara Oakley Sauer, Fremont, Wis.

[73] Assignee: Kimberly-Clark Worldwide, Inc., Neenah, Wis.

[21] Appl. No.: 08/668,106

[22] Filed: Jun. 19, 1996

[51] Int. Cl.[6] .................................................. A61F 13/15
[52] U.S. Cl. .................................. 604/385.2; 604/385.1; 604/386
[58] Field of Search .......................... 604/385.1, 385.2, 604/386, 393–399

[56] References Cited

U.S. PATENT DOCUMENTS

| 3,658,064 | 4/1972 | Pociluyko . | |
|---|---|---|---|
| 4,490,148 | 12/1984 | Beckestrom | 604/385 |
| 4,662,877 | 5/1987 | Williams . | |
| 4,663,220 | 5/1987 | Wisneski et al. | 428/221 |
| 4,681,580 | 7/1987 | Reising et al. . | |
| 4,701,171 | 10/1987 | Boland et al. . | |
| 4,704,116 | 11/1987 | Enloe . | |
| 4,738,677 | 4/1988 | Foreman . | |
| 4,743,246 | 5/1988 | Lawson . | |
| 4,753,646 | 6/1988 | Enloe . | |
| 4,798,603 | 1/1989 | Meyer et al. | 604/378 |
| 4,816,025 | 3/1989 | Foreman | 604/385.2 |
| 4,846,823 | 7/1989 | Enloe | 604/385.2 |
| 4,846,825 | 7/1989 | Enloe et al. | 604/385.1 |
| 4,892,536 | 1/1990 | DesMarais et al. | 604/385.2 |
| 4,895,568 | 1/1990 | Enloe | 604/385.2 |
| 4,938,753 | 7/1990 | Van Gompel et al. | 604/385.2 |
| 4,990,147 | 2/1991 | Freeland | 604/385.2 |
| 4,998,929 | 3/1991 | Bjorksund et al. | 604/385.2 |
| 5,019,066 | 5/1991 | Freeland et al. | 604/385.2 |
| 5,026,364 | 6/1991 | Robertson | 604/385.1 |
| 5,106,385 | 4/1992 | Allen et al. | 604/391 |
| 5,151,092 | 9/1992 | Buell et al. | 604/385.2 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. | 428/284 |
| 5,196,000 | 3/1993 | Clear et al. | 604/385.2 |
| 5,207,663 | 5/1993 | McQueen | 604/385.1 |

(List continued on next page.)

FOREIGN PATENT DOCUMENTS

| 0217032 A3 | 4/1987 | European Pat. Off. . |
|---|---|---|
| 0 433 951 | 6/1991 | European Pat. Off. . |
| 0692230 A1 | 1/1995 | European Pat. Off. . |
| 0 688 550 | 12/1995 | European Pat. Off. . |
| 0 715 840 | 6/1996 | European Pat. Off. . |
| 2 677 541 | 12/1992 | France . |
| 93/25171 | 12/1993 | WIPO . |
| 95/14453 | 6/1995 | WIPO . |
| 95/22951 | 8/1995 | WIPO . |
| 95/32697 | 12/1995 | WIPO . |
| 95/32698 | 12/1995 | WIPO . |
| 96/07381 | 3/1996 | WIPO . |
| 97/15260 | 5/1997 | WIPO . |

OTHER PUBLICATIONS

Patent Cooperation Treaty Search Report from the International Search Authority, International Application No. PCT/US 97/09754 dated Nov. 6, 1997.

Primary Examiner—John G. Weiss
Assistant Examiner—K. M. Reichle
Attorney, Agent, or Firm—Jeffrey B. Curtin

[57] ABSTRACT

An absorbent article includes an improved waist flap which includes a central zone and a pair of laterally opposed side zones which extend laterally outward from the central zone to the side edges of the absorbent article. The side zones of the waist flap are elasticized such that they are capable of being elongated in the lateral direction when the side edges of the absorbent article are extended to fasten the absorbent article about the waist of a wearer. The central zone of the waist flap may be substantially inelastic such that it conforms to the wearer's body and, in particular, to the small of the wearers back.

6 Claims, 6 Drawing Sheets

U.S. PATENT DOCUMENTS

| | | | |
|---|---|---|---|
| 5,221,274 | 6/1993 | Buell et al. | 604/385.2 |
| 5,226,992 | 7/1993 | Morman | 156/62.4 |
| 5,254,111 | 10/1993 | Cancio et al. | 604/385.1 |
| 5,269,775 | 12/1993 | Freeland et al. | 604/385.2 |
| 5,306,268 | 4/1994 | Enloe | 604/385.2 |
| 5,330,458 | 7/1994 | Buell et al. | 604/385.1 |
| 5,358,500 | 10/1994 | Lavon et al. | 604/385.2 |
| 5,368,584 | 11/1994 | Clear et al. | 604/385.2 |
| 5,397,318 | 3/1995 | Dreier | 604/385.2 |
| 5,415,644 | 5/1995 | Enloe | 604/385.2 |
| 5,500,063 | 3/1996 | Jessup | 604/385.2 |
| 5,507,736 | 4/1996 | Clear et al. | 604/385.2 |
| 5,509,915 | 4/1996 | Hanson et al. | 604/378 |
| 5,558,660 | 9/1996 | Dreier | 604/385.2 |
| 5,569,227 | 10/1996 | Vandemoortele et al. | 604/382 |

ABSORBENT ARTICLE HAVING A SELECTIVELY ELASTICIZED WAIST FLAP

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which are configured to absorb and contain body exudates and prevent leakage.

2. Description of the Related Art

Conventional absorbent articles, such as disposable diapers, employ absorbent materials located between a liquid pervious topsheet and a liquid impermeable backsheet to absorb body exudates. Such conventional absorbent articles have typically included elasticized waistbands and leg cuffs to help reduce the leakage of body exudates. Some conventional absorbent articles have also included elasticized containment or barrier flaps at the leg or waist sections of the article to further reduce leaks.

However, conventional absorbent articles which incorporate containment flaps at their waist sections have not been completely satisfactory. For example, it has been difficult to maintain the desired operation of the waist flap when the articles are being worn. To achieve a better fit, the waist flaps incorporated on conventional absorbent articles have typically been elasticized across the entire width or at least the central portion of the waist flap. However, it still has been difficult to maintain contact between the free edge of the waist flap and the wearer's body and reliably hold the flap open for an effective receipt and containment of urine and feces. This is particularly true across the back waist region of the absorbent article due to the typical configuration of the wearer's lower back region which is generally referred to as the small of the back. For example, the back of the wearer is typically concave or flat and, as such, it has been difficult to maintain contact with such a region.

Moreover, since the absorbent article is typically fastened upon the wearer when the wearer is lying on their back and on the back portion of the absorbent article, it has been difficult to correctly elongate and position any type of a back waist flap on the initial fastening of the absorbent article to the wearer. Such difficulties encountered in obtaining the optimum fit of the back waist flap about the wearer have undesirably resulted in increased leakage. As a result, conventional absorbent articles having back waist flaps have not been completely satisfactory. Accordingly, there remains a need for improved containment at the waist sections and, in particular, at the back waist section, of absorbent articles.

SUMMARY OF THE INVENTION

In response to the difficulties and problems discussed above, a new disposable absorbent article which has an improved waist flap has been discovered.

In one aspect, the present invention relates to an absorbent article which defines a front waist section, a rear waist section, an intermediate section which interconnects said front and rear waist sections, a pair of longitudinally opposed end edges, and a pair of laterally opposed side edges. The absorbent article comprises a waist flap which is attached adjacent one of said end edges of said absorbent article in one of said waist sections. The waist flap extends inwardly towards the intermediate section to create a pocket between the waist flap and the waist section of the absorbent article. The waist flap defines a central zone and a pair of laterally opposed side zones which are connected to and extend outwardly in a lateral direction from the central zone to the side edges of the absorbent article. The side zones are configured to elongate in the lateral direction at least about 25 percent more than the central zone of the waist flap when the side edges of the absorbent article are extended outwardly in the lateral direction. In a particular aspect, the central zone of the waist flap is centered about a longitudinal centerline of the absorbent article and defines a width which is at least about 20 percent of a width of the absorbent article at the respective waist section.

In another aspect, the present invention relates to an absorbent article which defines a front waist section, a rear waist section, an intermediate section which interconnects the front and rear waist sections, a pair of longitudinally opposed end edges, and a pair of laterally opposed side edges. The absorbent article comprises a rear waist flap which defines a central zone which is capable of being elongated in a lateral direction from 0 to about 50 percent from a relaxed condition and a pair of laterally opposed side zones which extend outwardly in the lateral direction from the central zone to the side edges of the absorbent article. Each side zone is capable of being elongated in the lateral direction from about 50 to about 350 percent from a relaxed condition. The rear waist flap also defines an attached edge which is attached to the absorbent article adjacent the end edge and the side edges of the absorbent article in the rear waist section and a free edge which remains unattached to and spaced apart from the rear waist section of the absorbent article in at least the central zone to define a pocket between the rear waist flap and the rear waist section of the absorbent article.

In still another aspect, the present invention relates to an absorbent article which defines a front waist section, a rear waist section, an intermediate section which interconnects the front and rear waist sections, a pair of longitudinally opposed end edges, and a pair of laterally opposed side edges. The absorbent article comprises a backsheet layer, a liquid permeable topsheet layer which is connected in superposed relation to the backsheet layer, an absorbent body which is located between the topsheet layer and the backsheet layer, and a rear waist flap which is attached adjacent the end edge and the opposed side edges of the absorbent article in the rear waist section. The rear waist flap extends inwardly towards the intermediate section to create a pocket between the rear waist flap and the topsheet layer of the absorbent article for containing body exudates. At least a portion of the rear waist flap adjacent the side edges of the absorbent article is capable of being elongated in a lateral direction at least about 50 percent from a relaxed condition. The absorbent article may further comprise a pair of fasteners which are connected to the rear waist flap along the side edges of the absorbent article. The fasteners are configured to connect the front and rear waist sections of the absorbent article about the waist of a wearer when in use.

In another aspect, the present invention relates to an absorbent article which defines a front waist section, a rear waist section, an intermediate section which interconnects the front and rear waist sections, a pair of longitudinally opposed end edges, and a pair of laterally opposed side edges. The absorbent article comprises a rear waist flap which is attached adjacent the end edge of the absorbent article in the rear waist section and which extends inwardly towards the intermediate section to create a pocket between the rear waist flap and the rear waist section. The rear waist flap defines a substantially inelastic central zone and a pair of laterally opposed, elasticized side zones which are connected to and extend outwardly in a lateral direction from the central zone to the side edges of the absorbent article.

In yet another aspect, the present invention relates to an absorbent article which defines a front waist section, a rear waist section, an intermediate section which interconnects the front and rear waist sections, a pair of longitudinally opposed end edges, and a pair of laterally opposed side edges. The absorbent article comprises a backsheet layer, a liquid permeable topsheet layer which is connected in superposed relation to the backsheet layer, an absorbent body which is located between the topsheet layer and the backsheet layer, and a rear waist flap which is attached adjacent the end edge and the side edges of the absorbent article in the rear waist section. The rear waist flap extends inwardly towards the intermediate section to create a pocket between the rear waist flap and the topsheet layer of the absorbent article for containing body exudates. The rear waist flap defines a central zone and a pair of laterally opposed, elasticized side zones which are connected to and extend outwardly in a lateral direction from the central zone to the side edges of the absorbent article. The absorbent article further comprises a spacer which is located between the rear waist flap and the topsheet layer in the central zone of the rear waist flap. The spacer is configured to maintain a free edge of the rear waist flap in a spaced apart relationship from the topsheet layer to provide the pocket. The spacer is located along a longitudinal centerline of the absorbent article and configured to press the rear waist flap into a sealing relationship with a gluteal fold on a wearer's body.

The present invention advantageously provides an absorbent article with an improved rear waist flap for better containment of body exudates and, in particular, runny fecal material. For example, the present invention provides a rear waist flap which is easily elongated and positioned about the back waist region of the wearer even when the wearer is lying on their back on the rear waist section of the article. Moreover, the present invention provides a rear waist flap which is elasticized such that it maintains a closer fit about the back region of the wearer. Such a closer, more optimum fit results in the absorbent article of the present invention being less susceptible to the leakage of body exudates when compared to conventional absorbent articles having waist flaps. Further, the present invention provides a waist flap construction which can more reliably and effectively maintain an open position to receive body exudates when the article is being worn. Such an open position is maintained while providing a tight seal in the gluteal fold of the wearer's body without causing an excessive irritation of the wearers skin. As a result, the present invention provides an absorbent article which has an improved waist containment flap to help reduce leakage.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

Figure 1:
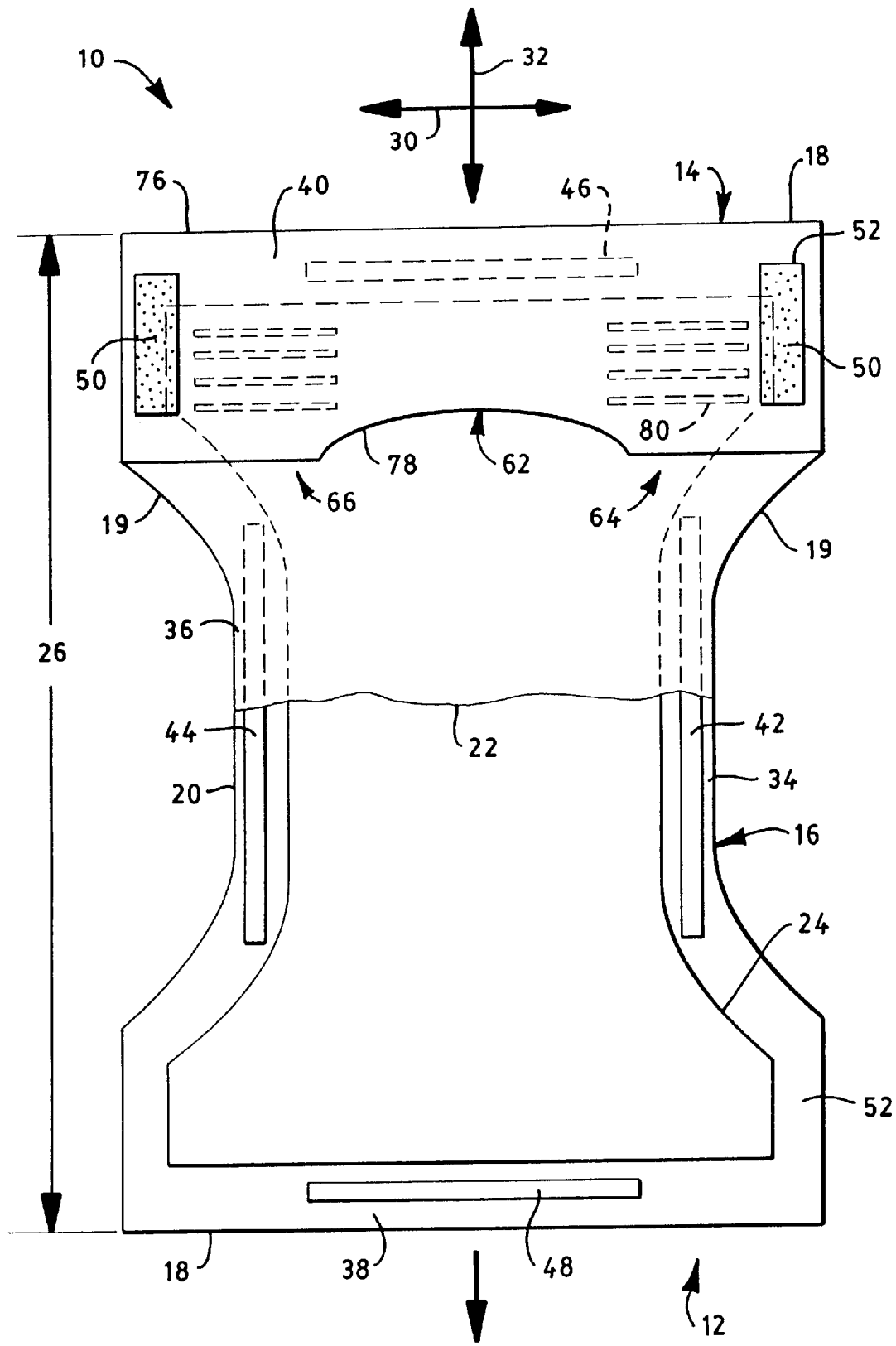
FIG. 1 representatively shows a partially cut away, top plan view of an absorbent article according to one embodiment of the invention.

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. The invention will be described in the context of its various configurations. It should be appreciated that alternative arrangements of the invention can comprise any combination of such configurations.

With reference to FIGS. 1–4, an integral absorbent garment article, such as the disposable diaper 10, generally defines a front waist section 12, a rear waist section 14, an intermediate section 16 which interconnects the front and rear waist sections, a pair of longitudinally opposed end edges 18, and a pair of laterally opposed side edges 19. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 19 define leg openings for the diaper and generally are curvilinear or contoured to more closely fit the legs of the wearer. The opposed end edges 18 define a waist opening for the diaper and typically are straight but may also be curvilinear.

FIG. 1 is a representative plan view of the diaper 10 of the present invention in a flat, uncontracted state. Portions of the structure of the diaper are partially cut away to more clearly show the interior construction of the diaper 10, and the surface of the diaper which contacts the wearer is facing the viewer. The diaper 10 includes a substantially liquid impermeable backsheet 20, a porous, liquid permeable topsheet 22 positioned in facing relation with the backsheet 20, and an absorbent body 24, such as an absorbent pad, which is located between the backsheet and the topsheet. The diaper 10 also defines a length 26, a width 28, a lateral direction 30, and a longitudinal direction 32 which, in the illustrated embodiments, defines a longitudinal centerline of the diaper.

The backsheet 20 defines a length and a width which, in the illustrated embodiments, generally coincides with the length 26 and width 28 of the diaper 10. The absorbent body 24 generally has a length and width which are less than the length and width of the backsheet 20. Marginal portions of the diaper 10, such as marginal sections of the backsheet 20, may extend past the terminal edges of the absorbent body 24. In the illustrated embodiment, for example, the backsheet 20 extends outwardly beyond the terminal marginal edges of the absorbent body 24 to form side margins 34 and 36 and end margins 38 and 40 of the diaper 10. The topsheet 22 is generally coextensive with the backsheet 20 but may optionally cover an area which is larger or smaller than the area of the backsheet 20, as desired.

Figure 2:
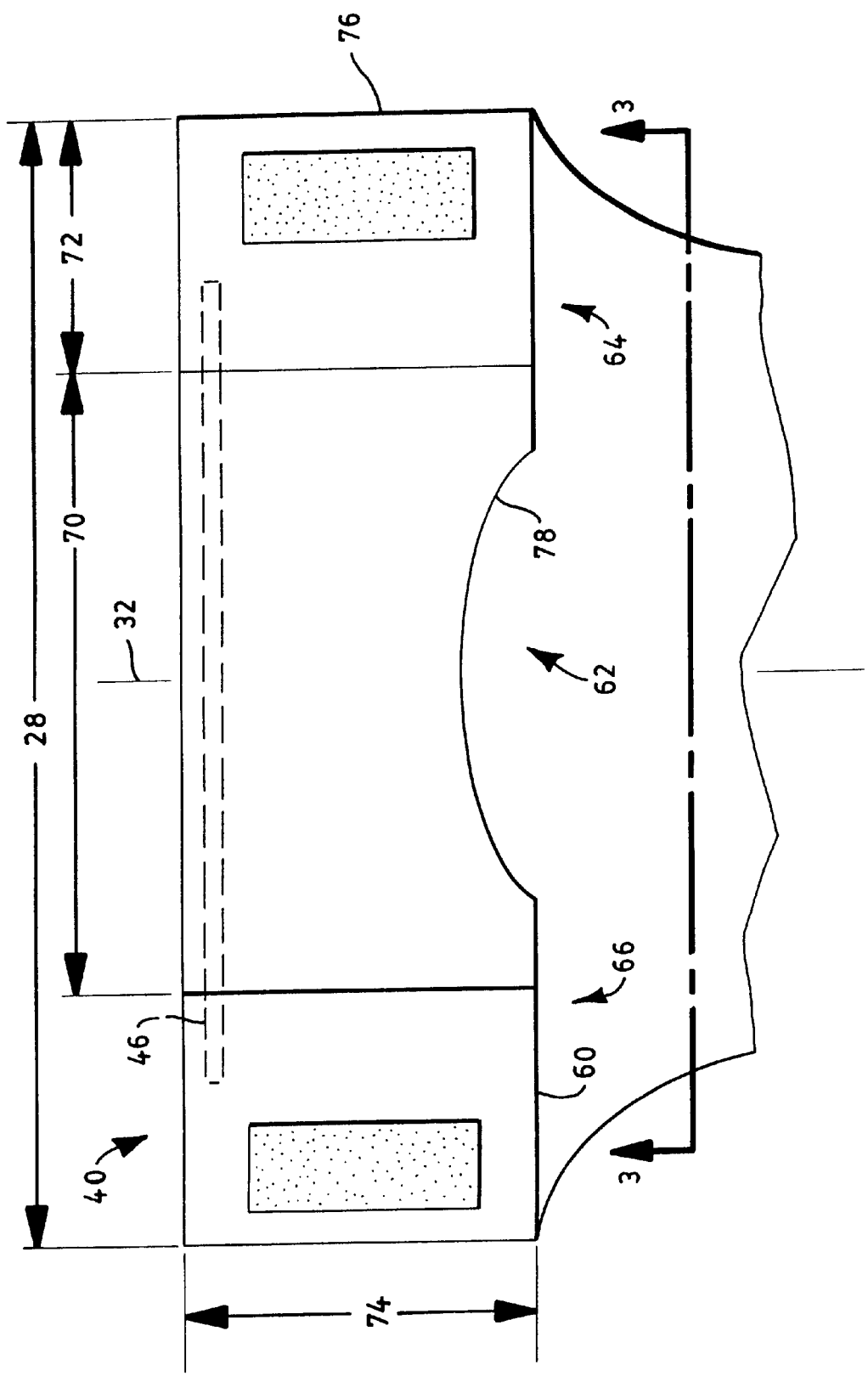
FIG. 2 representatively shows a top plan view of the back waist flap of the absorbent article of FIG. 1.
Figure 3:
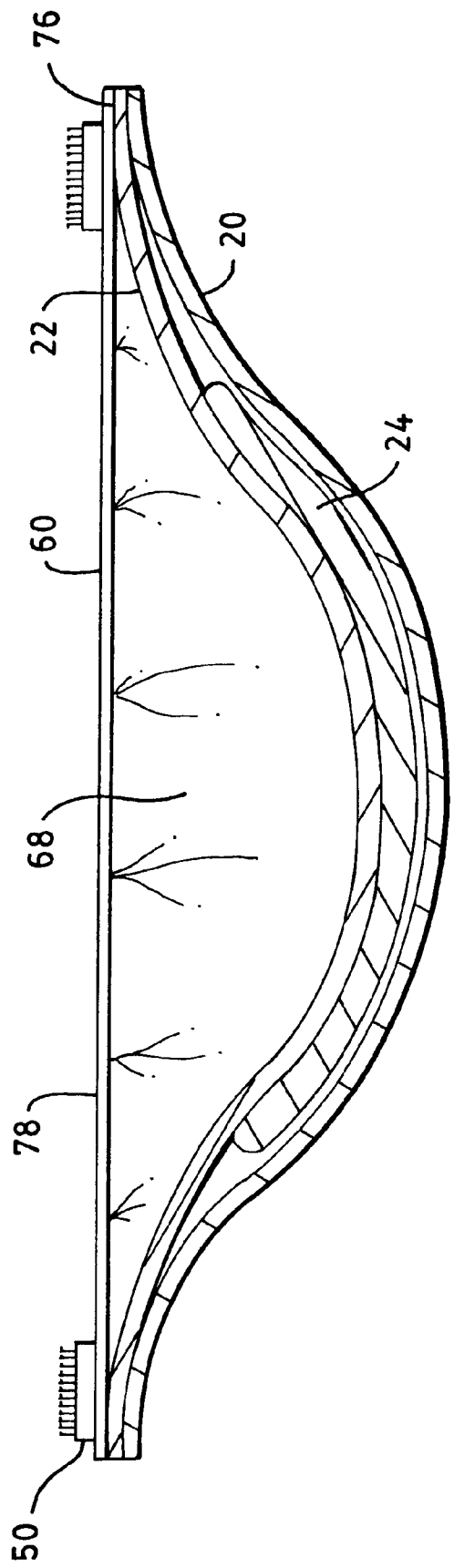
FIG. 3 representatively shows a sectional view of the absorbent article of FIGS. 1 and 2 taken along line 3—3 of FIG. 2.
Figure 4:
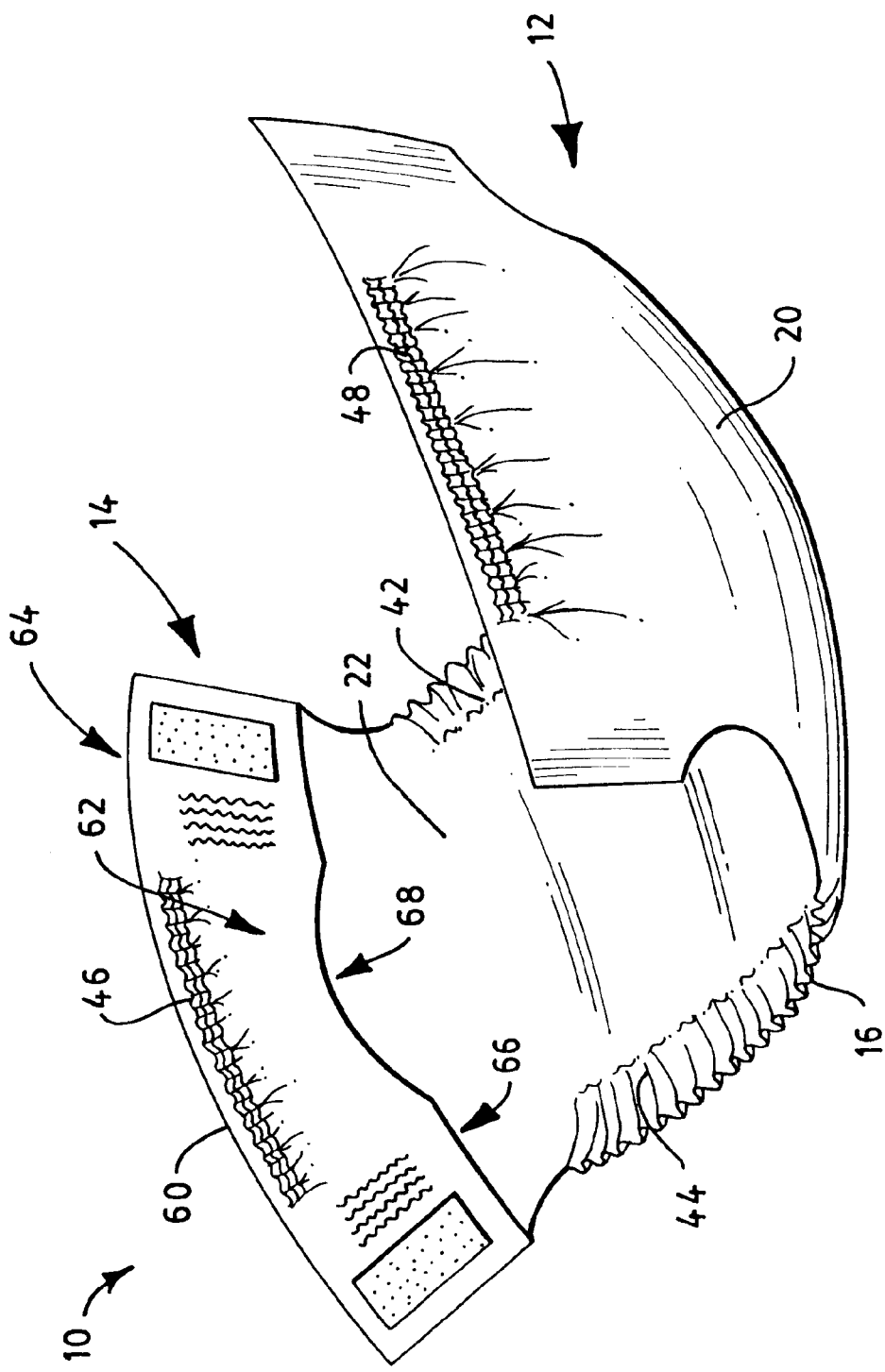
FIG. 4 representatively shows a perspective view of the absorbent article of FIG. 1 as it is generally configured in use.

To provide improved fit and to help reduce leakage of body exudates from the diaper 10, the side margins 34 and 36 and end margins 38 and 40 of the diaper may be elasticized with suitable elastic members, such as single or multiple strands of elastic. The elastic strands may be composed of natural or synthetic rubber and may optionally be heat shrinkable or heat elasticizable. Elastic members 42 and 44 are constructed to operably gather and shirr the side margins 34 and 36 of the diaper 10 to provide elasticized leg bands which can closely fit around the legs of the wearer to reduce leakage and provide improved comfort and appearance. Similarly, waist elastic members 46 and 48 can be employed to elasticize the end margins 38 and 40 of the diaper 10 to provide elasticized waistbands. The waist elastics are configured to operably gather and shirr the waistband sections to provide a resilient, comfortably close fit around the waist of the wearer. In FIGS. 1–3, the elastic members are illustrated in their uncontracted, stretched condition for the purpose of clarity.

Fastening means, such as fasteners 50, such as hook-and-loop fasteners, are employed to secure the diaper on a wearer. Alternatively, other fastening means, such as buttons, pins, snaps, adhesive tape fasteners, mushroom-and-loop fasteners, or the like, may be employed. A cooperating side panel member (not shown) can be associated with each fastener and may be constructed to be nonelastic or elastically stretchable. For example, the fasteners 50 may be attached to a side panel member which is then attached to the side edges of the waist flap.

The illustrated embodiment of the diaper 10 includes ear portions 52 which extend laterally along the diaper cross-direction 30 and are positioned at least at the rear waist section 14 of the diaper 10. Ear portions 52 may also be located at the front waist section 12 of the diaper. The ear portions may be integral with the backsheet 20 or may comprise separate sections which are composed of the same or different material than the backsheet 20 and are suitably assembled and attached to the backsheet 20.

The diaper 10 further includes at least one waist flap 60 which is attached adjacent an end edge of the absorbent article. The waist flap 60 extends inwardly towards the intermediate section 16 of the diaper article to provide a pocket 68 between the free edge 78 of the waist flap 60 and the topsheet 22 in the waist section of the diaper 10 for containing body exudates and, in particular, runny fecal material.

The diaper 10 may also include a pair of elasticized, longitudinally extending containment flaps (not shown) which are configured to maintain an upright, perpendicular arrangement in at least the intermediate section 16 of the diaper 10 to serve as an additional barrier to the lateral flow of body exudates. The diaper 10 may further include a surge management layer (not shown) positioned between the topsheet 22 and the absorbent body 24 which is configured to efficiently hold and distribute liquid exudates to the absorbent body 24. The surge management layer can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 10 may be of various suitable shapes. For example, the diaper may have an overall rectangular shape, T-shape or an approximately hour-glass shape. In the shown embodiment, the diaper 10 has a generally I-shape. Other suitable diaper components which may be incorporated on absorbent articles of the present invention include containment flaps, elastomeric side panels, and the like.

Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. patent application Ser. No. 08/096,654 filed Jul. 22, 1993, in the name of Hanson et al., the disclosures of which are herein incorporated by reference to the extent they are consistent herewith.

The various components of the diaper 10 are integrally assembled together employing various types of suitable attachment means, such as adhesive, sonic bonds, thermal bonds or combinations thereof. In the shown embodiment, for example, the topsheet 22 and backsheet 20 are assembled to each other and to the absorbent body 24 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 42, 44, 46, and 48 and the fasteners 50, may be assembled into the diaper 10 article by employing the above-identified attachment mechanisms.

The backsheet 20 of the diaper 10, as representatively illustrated in FIGS. 1–4, may suitably be composed of a material which is either liquid permeable or liquid impermeable. It is generally preferred that the backsheet 20 be formed from a material which is substantially impermeable to liquids. For example, a typical backsheet can be manufactured from a thin plastic film or other flexible liquid-impermeable material. For example, the backsheet 20 may be formed from a polyethylene film having a thickness of from about 0.012 millimeter (0.5 mil) to about 0.051 millimeter (2.0 mils). If it is desired to present the backsheet with a more clothlike feeling, the backsheet 20 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike backsheets are known to those skilled in the art.

Further, the backsheet 20 may be formed of a woven or nonwoven fibrous web layer which has been totally or partially constructed or treated to impart a desired level of liquid impermeability to selected regions that are adjacent or proximate the absorbent body 24. Still further, the backsheet 20 may optionally be composed of a micro-porous "breathable" material which permits vapors to escape from the absorbent body 24 while still preventing liquid exudates from passing through the backsheet 20. The backsheet 20 typically provides the outer cover of the diaper 10. The backsheet 20 can also be embossed or otherwise provided with a matte finish to provide a more aesthetically pleasing appearance.

The topsheet 22, as representatively illustrated in FIGS. 1–4, suitably presents a bodyfacing surface which is compliant, soft feeling, and nonirritating to the wearer's skin. Further, the topsheet 22 may be less hydrophilic than the absorbent body 24, to present a relatively dry surface to the wearer, and may be sufficiently porous to be liquid permeable, permitting liquid to readily penetrate through its thickness. A suitable topsheet 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 22 is suitably employed to help isolate the wearer's skin from liquids held in the absorbent body 24.

Various woven and nonwoven fabrics can be used for the topsheet 22. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 22 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation TRITON X-102. The surfactant may be applied by any conventional means, such as spraying, printing, brush coating or the like. The surfactant may be applied to the entire topsheet 22 or may be selectively applied to particular sections of the topsheet 22, such as the medial section along the longitudinal centerline of the diaper, to provide greater wettability of such sections.

The absorbent body 24 of the diaper 10, as representatively illustrated in FIGS. 1–4, may suitably comprise a matrix of hydrophilic fibers, such as a web of cellulosic fluff, mixed with particles of a high-absorbency material commonly known as superabsorbent material. In a particular embodiment, the absorbent body 24 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 24 to better contain and absorb body exudates. The concentration of the superabsorbent particles may also vary through the thickness of the absorbent body 24. Alternatively, the absorbent body 24 may comprise a laminate of fibrous webs and superabsorbent material or other suitable means of maintaining a superabsorbent material in a localized area.

The absorbent body 24 may have any of a number of shapes. For example, the absorbent core may be rectangular, I-shaped, or T-shaped. It is generally preferred that the absorbent body 24 be narrower in the crotch area than in the front or rear portions of the diaper 10. The size and the absorbent capacity of the absorbent body 24 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 24.

Optionally, a substantially hydrophilic tissue wrapsheet (not illustrated) may be employed to help maintain the integrity of the airlaid fibrous structure of the absorbent body 24. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The waist flap 60 of the diaper 10 of the present invention, as representatively illustrated in FIGS. 1–4, is designed to contain and prevent the leakage of body exudates from the end edges 18 of the diaper 10. In a particularly desirable embodiment, the waist flap 60 is located in the rear waist section 14 of the diaper to contain runny fecal material. The waist flap 60 is also designed to maintain the article in contact with the wearer while allowing the other portions of the absorbent article to blouse away from the wearer thereby creating void volume to contain body exudates.

The waist flap 60 may be provided in a variety of ways. For example, the waist flap 60 may be an integral portion of the backsheet 20 or topsheet 22 or may be a separate layer or a combination of separate layers which are attached to the absorbent article using conventional attachment mechanisms such as those described above. In the illustrated embodiment, the waist flap 60 comprises a separate layer which includes an attached edge 76 which is attached to the end edge 18 and opposed side edges 19 of the diaper 10 in the rear waist section 14 of the diaper 10 using adhesive bonds. The waist flap 60 also includes a free edge 78 which extends inwardly towards the intermediate section 16 of the diaper 10. The free edge 78 of the waist flap 60 is configured to remain in a spaced apart relation from the topsheet 22 of the diaper 10 when in use to provide a pocket 68 having an opening for receiving and containing body exudates. The free edge 78 desirably remains unattached to the respective waist section in at leas the central zone 62 of the waits flap 60. The pocket 68 formed by the waist flap 60 is particularly well suited for containing fecal material.

The waist flap 60 of the diaper 10, as representatively illustrated in FIGS. 1–4, may suitably be composed of a material which is either liquid permeable or liquid impermeable. For example, the waist flap 60 may be composed of materials described above as being suitable for the backsheet 20 or topsheet 22. Alternatively, the waist flap 60 may include two or more different materials which may be joined together or otherwise arranged to provide different portions of the waist flap with different characteristics or properties such as, for example, different elastic properties.

It is generally preferred that the waist flap 60 be formed from a material which is substantially impermeable to liquids and which provides a more clothlike feeling. Such a material is capable of containing body exudates while not irritating the skin of the wearer. For example, a typical waist flap 60 can be manufactured from a polyethylene film having a nonwoven web laminated to the outer surface thereof, such as a spunbond web of polyolefin fibers. The waist flap 60 may also be formed of a woven or nonwoven fibrous web layer which has been totally or partially constructed or treated to impart a desired level of liquid impermeability, or wettability and hydrophilicity. Still further, the waist flap 60 may optionally be composed of a micro-porous "breathable" material which permits vapors to escape from the pocket 68 between the waist flap 60 and the topsheet 22 of the diaper 10 while still preventing liquid exudates from passing through the waist flap 60.

It is also desirable that the outer surface or bodyfacing surface of the waist flap 60 be at least partially wettable or hydrophilic to at least partially absorb any body exudates which become trapped between the waist flap and the skin of the wearer. A particular well suited nonwoven web for such a configuration is a hydrophilic nonwoven material which is commercially available from E. I. Dupont de Nemours, a business having offices located in Wilmington, Del., under the trade designation SONTARA 8423. It is further desirable that the nonwoven material have its fibers oriented in a predetermined direction such that the material can be positioned on the diaper 10 with the fibers oriented in the lateral direction 30. For example, the waist flap may be made from a machine direction oriented nonwoven material. As a result, any body exudates which are forced between the waist flap 60 and the skin of the wearer are directed in the lateral direction 30 towards the side edges 19 of the absorbent article and away from the end edges 18. For example, in a particular embodiment, the nonwoven material may include at least about 50 percent rayon fibers which have been oriented in the lateral direction 30.

The waist flap 60 generally extends laterally across the diaper 10 and accordingly has a width which generally corresponds to the width 28 of the diaper 10 at the respective waist section to which the waist flap 60 is attached. As used herein, the width of the diaper 10 refers to the dimension between the outermost portions of the backsheet and/or topsheet layer in the lateral direction 30 at the desired lengthwise location along the diaper 10. The waist flap 60 also defines a length 74 which is desirably from about 10 to about 30 percent of the length 26 of the diaper 10. For example, the waist flap 60 may define a length 74 of from about 0.5 to about 4.0 inches. Lengths less than the above specified ranges do not provide enough void volume space to contain body exudates. Whereas, lengths greater than the above specified ranges may extend too far into the intermediate section 16 of the diaper 10 such that the waist flap 60 may interfere with the deposition of body exudates into the diaper article. If the length of the waist flap 60 is too great, it may also be subjected to pressure from the wearer when the wearer sits thus eliminating at least a portion of the void space created by the pocket 68.

In the illustrated embodiments, the waist flap 60 generally defines a central zone 62 which is flanked by a pair of laterally opposed side zones 64 and 66. The side zones 64 and 66 are connected to and extend outwardly in a lateral direction 30 from the central zone 62 to the side edges 19 of the diaper 10. In use, the central zone 62 is generally configured to be located on the front abdominal or back regions of the wearer while the side zones 64 are generally configured to be located on the side hip/buttock regions of the wearer. When the waist flap 60 is located in the rear waist section of the article, the side zones 64 and 66 are configured to be more elastic or stretchable in the lateral direction 30 than the central zone 62 to provide a more optimum fit and seal about the back region of the wearer. Whereas, when the waist flap 60 is located in the front waist section of the article, the side zones 64 and 66 are configured to be less elastic or stretchable in the lateral direction 30 than the central zone 62 to provide a more optimum fit and seal about the front abdominal region of the wearer.

On the majority of typical wearers of such absorbent articles and, in particular, on infants, the small or central portion of the wearer's back is generally concave (bowed inwards) or flat in shape. The elastic on conventional absorbent articles which have included waist elastics typically spans across the concave shape of the back such that a gap may form between the wearer and the article. As a result, it has been difficult to maintain a tight seal between the absorbent article and the wearer in this area. When the waist flap 60 of the present invention is located in the rear waist section 14 of the diaper 10, the central zone 62 of the waist flap 60 corresponds to the area of the waist flap 60 which is intended to be in contact with the small of the wearer's back when in use. In such a configuration, the central zone 62 of the waist flap 60 also corresponds to that portion of the diaper 10 on which the wearer is placed when securing the diaper article about the waist of the wearer. The waist flap 60 of the present invention is designed to provide an optimum fit and seal between the waist flap and the wearer which can be properly secured in the correct position on the initial securing of the diaper 10 on the wearer.

As representatively illustrated in FIG. 2, the central zone 62 of the waist flap 60 is typically centered about the longitudinal centerline 32 of the diaper 10 and defines a width 70 which generally corresponds to the width of the small of the wearer's back. For example, the width 70 of the central zone 62 of the waist flap 60 may be from about 10 to about 80 percent and desirably from about 25 to about 70 percent of the width of the diaper 10. In a particular embodiment, the width 70 of the central zone 62 of the waist flap 60 is at least about 10 percent, desirably at least about 20 percent, and more desirably at least about 30 percent of the width 28 of the diaper 10. For example, the width 70 of the central zone 62 of the waist flap 60 on a diaper article which is intended to be worn by a medium-sized infant may be from about 5 to about 15 centimeters. Width dimensions less than the above specified ranges are not sufficient to extend along the entire width of the small of the wearer's back.

In the illustrated embodiments, the central zone 62 of the waist flap 60 is configured to have a relatively low level of stretchability and be subjected to relatively low levels of tension in the lateral direction 30 such that the free edge 78 of the waist flap 60 in the central zone 62 can more readily configure itself to the shape of the wearer's back to provide a tight seal. For example, the central zone 62 is capable of being elongated in the lateral direction 30 no more than about 100 percent, desirably no more than about 50 percent, and more desirably no more than about 25 percent from a relaxed condition. In a particular embodiment, the central zone 62 is capable of being elongated in the lateral direction 30 from 0 to about 50 percent from a relaxed condition. It has been discovered that when the central zone 62 is capable of elongating more than the amounts set forth above, the tension on the free edge 78 of the waist flap 60 tends to force the free edge 78 to bridge across the small of the wearer's back thereby providing an opening between the waist flap 60 and the wearer through which body exudates may leak. In a particularly desirable configuration, the central zone 62 of the waist flap 60 is substantially incapable of being elongated in the lateral direction 30. As representatively illustrated in FIGS. 1–4, the free edge 78 of the waist flap 60 may be curvilinear, such as concave, to better fit the wearer in the small of the back.

The side zones 64 and 66 of the waist flap 60 are generally the area of the waist flap 60 which are intended to be in contact with the convex surface of the outer back hip/buttock regions of the wearer when in use. As representatively illustrated in FIG. 2, the side zones 64 and 66 of the waist flap 60 laterally flank the central zone 62 of the waist flap 60 and generally extend to the side edges 19 of the diaper 10. Each of the side zones 64 and 66 defines a width 72 which generally corresponds to the width of the portions of the diaper article which are intended to be positioned on the hip/buttock regions of the wearer in use. For example, the width 72 of each side zone 64 and 66 of the waist flap 60 may be from about 10 to about 45 percent and desirably from about 15 to about 30 percent of the width 28 of the diaper 10 at the respective waist section to which the waist flap is attached. If the absorbent article includes a pair of longitudinally extending containment flaps, it is desirable that the side zones 64 of the waist flap 60 extend laterally inwardly at least to the respective containment flap for improved performance.

The side zones 64 and 66 of the waist flap 60 are configured to elongate in the lateral direction when the diaper article is fit about the hips of a wearer and fastened thereto. Specifically, the side zones 64 and 66 are configured to exert a force against the convex surface of the outer back hip/buttock regions of the wearer to provide a close-to-the body fit. The elongation of the side zones 64 and 66 of the waist flap 60 also assist in maintaining the free edge 78 of the waist flap 60 in a spaced apart relation from the topsheet 22 of the diaper 10. Generally, each side zone 64 and 66 is capable of being elongated in the lateral direction 30 from about 50 to about 350 percent and desirably from about 100 to about 300 percent from a relaxed condition for improved performance. In a particular embodiment, each side zone 64 and 66 is capable of being elongated in the lateral direction 30 at least about 50 percent, desirably at least about 100 percent, and more desirably at least about 200 percent from a relaxed condition. It has been discovered that when each side zone 64 and 66 is not capable of elongating the amounts set forth, the waist flap 60 may not provide a close seal about the wearer's hips and the free edge 78 of the waist flap 60 may not maintain a spaced apart relation from the topsheet 22 of the diaper article when in use thereby undesirably resulting in increased leakage.

In the illustrated embodiments, each side zone 64 and 66 of the waist flap 60 is configured to elongate a greater percentage than the central zone 62 of the waist flap 60 when the side edges 19 of the diaper 10 are extended in the lateral direction 30 to position and fasten the diaper about the waist of a wearer. In a particular embodiment, each of the side zones 64 and 66 of the waist flap 60 is elongated at least about 25 percent, desirably at least about 50 percent, and more desirably at least about 100 percent more than the central zone 62 of the waist flap 60 when the side edges 19 of the diaper 10 are extended in the lateral direction 30. In a particular embodiment, the central zone 62 is capable of being elongated no more than about 50 percent and each side zone is capable of elongating at least about 100 percent from a relaxed condition for improved performance. The above recited elongations of the zones 62, 64, and 66 provide an improved fit about the wearer and an improved seal between the free edge 78 of the waist flap 60 and the wearer's body.

It is also hypothesized that waist flaps having such differential stretchability between the central zone and side zones thereof as set forth above would be easier to fasten about a wearer. To fasten conventional absorbent articles about a wearer, the wearer typically is placed back down on the rear waist portion of the absorbent article and the front waist portion is brought upward between the legs of the wearer and positioned on the front abdominal region of the wearer. The side edges of the absorbent article at the front and rear waist sections are then fastened together to secure the article on the wearer. It is theorized that moving the location of the stretchable portions of the waist flap 60 from the center of the article to it's side edges improves the positioning and fastening of the article about the wearer which provides an optimum fit and reduces leaks. Such improvements are realized because the portions of the waist flap 60 which are configured to stretch, the side zones 64 and 66 of the waist flap 60 of the present invention, are not subjected to the weight of the wearer in the fastening process. Whereas, in conventional absorbent articles which have included rear waist flaps having elastic portions across the center of the flap and article, the weight of the wearer on the elastic portions has adversely affected the ability to elongate the elastics to properly position and fasten the article about the wearer on the initial fastening.

In a particular embodiment, each of the side zones 64 and 66 of the waist flap 60 may be configured to provide variable levels of elongation in the lateral direction 30 along its length 74 to better fit the intended wearer. For example, the portion of each of the side zones 64 and 66 adjacent the free edge 78 of the waist flap 60 may be capable of elongating a greater percentage than the portions of each side zone adjacent the respective end edge 18 of the absorbent article. In such a configuration, the elongation of the side zones 64 and 66 near the free edge 78 may help maintain the pocket 68 in an open position to receive body exudates. Alternatively, the portion of each of the side zones 64 and 66 adjacent the end edge 18 of the absorbent article may be capable of elongating a greater percentage than the portions of each side zone adjacent the free edge 78 of the waist flap. It is hypothesized that such a configuration may provide a better fit on older infants because the side zones 64 and 66 are allowed to extend around the buttocks region of older infants which tends to extend further outward. In addition, the longitudinal mid-portion of each of the side zones 64 and 66 may be capable of elongating a different percentage than the portions of the side zones adjacent the free edge 78 of the waist flap 60 and end edge 18 of the absorbent article.

The side zones 64 and 66 of the waist flap 60 may be made stretchable by means well known to those skilled in the art. For example, as representatively illustrated in FIG. 1, each of the side zones 64 and 66 may include a plurality of elastic strands 80. In such a configuration, the elastic strands 80 are elongated and attached in the lateral direction 30 to the side zones 64 and 66 of the waist flap 60. The elastic strands 80 may also be sandwiched between the waist flap 60 and a second material before being attached to the waist flap 60. In a particular embodiment, the elastic strands 80 are adhesively attached to the side zones 64 and 66 of the waist flap 60 at an elongation of from about 25 to about 350 percent, desirably from about 50 to about 300 percent, and more desirably from about 100 to about 250 percent from a relaxed position. In a particularly desirably embodiment, the elastic stands 80 are adhesively attached to the side zones at an elongation of at least about 100 percent. When the elastic strands 80 are elongated less than such amounts, the side zones 64 and 66 may not effectively maintain the free edge 78 of the waist flap 60 in a spaced apart relation from the topsheet 22 and maintain the diaper 10 about the waist of the wearer in use. The elastic strands 80 on each side zone 64 and 66 may further be elongated variable amounts before being attached to the side zones to provide each side zone with variable elongation along its length as discussed above.

Any suitable number of elastic strands 80 which provide the desired stretchability may be attached to the side zones 64 and 66. For example, each side zone 64 and 66 of the waist flap 60 may include from about 2 to about 10 elastic strands 80 which are elongated in the lateral direction 30 and attached to the rear waist flap 60 in the elongated condition. Suitable elastic strands 80 for use on the side zones 64 and 66 of the waist flap 60 are known to those skilled in the art. For example, a suitable elastic strand 80 may be composed of a 470 decitex LYCRA elastomer or a 620 decitex LYCRA elastomer commercially available from E. I. DuPont de Nemours Co., a business having offices located in Wilmington, Del., or other elastomers with suitable characteristics.

In an alternative embodiment, an elastic material may be attached to each of the side zones 64 and 66 of the waist flap 60 in an elongated condition to provide the desired stretchability. The elastic material may include a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220, issued May 5, 1987 to T. Wisneski et al., the disclosure of which is hereby incorporated by reference. Examples of composite fabrics comprising at least one layer of a nonwoven material secured to a fibrous elastic layer are described in European Patent Application NO. EP 0 110 010 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to Mormon, the disclosure of which is hereby incorporated by reference. In a particular embodiment, the elastic composite material is adhesively attached to the side zones 64 and 66 of the waist flap 60 at an elongation of from about 25 to about 350 percent, desirably from about 50 to about 300 percent, and more desirably from about 100 to about 250 percent from a relaxed position. In a particularly desirably embodiment, the elastic composite material is adhesively attached to the side zones at an elongation of at least about 100 percent to provide improved performance.

In still another alternative embodiment, the central zone 62 and side zones 64 and 66 may be provided by three individual pieces of material which are joined together along their side edges to provide the waist flap 60. For example, the central zone 62 may include any of the materials described above as being suitable for the waist flap 60 and the side zones 64 and 66 may include elastic materials which provide the desired stretchability. The elastic materials may include a stretch-bonded-laminate (SBL) material, a neck-bonded-laminate (NBL) material, an elastomeric film, an elastomeric foam material, or the like as described above. The individual pieces may also include a pair of conventional nonwoven webs in a facing relationship having elastic threads adhesive laminated therebetween.

The waist flap 60 may also be elongated prior to being attached to the article to effectively retract the side edges of the article. For example, the waist flap 60 may be elongated in the lateral direction from about 25 to about 350 percent and desirably from about 50 to about 300 percent before being attached to the side edges of the absorbent article.

As representatively illustrated in FIGS. 1–4, the diaper 10 may further include a rear waist elastic 46. The rear waist elastic 46 is intended to gather and shirr the end edge 18 of the diaper 10 at the rear waist section 14 to help provide a more tailored appearance and reduce the incidence of leaks. The rear waist elastic 46 is attached adjacent the end edge 18 in a laterally elongated condition. The rear waist elastic 46 may be attached to the backsheet 20, topsheet 22 or waist flap 60 adjacent the end edge. However, it is generally desirable that the rear waist elastic 46 be attached to the waist flap 60 for ease of processing.

It is desirable that the rear waist elastic element 46 be attached at an elongation which is less than the elongation at which the elastic elements are attached to the side zones 64 and 66 of the waist flap 60. As a result, when the side edges 19 of the diaper 10 are extended in the lateral direction 30, the majority of the elongation and stretch occurs across the side zones 64 and 66 of the waist flap 60. Such differences in elongation at attachment ensures that the free edge 78 of the waist flap 60 maintains a spaced apart relation from the topsheet 22 to provide the pocket 68 for containing exudates. In a particular embodiment, the rear waist elastic 46 is elongated no more than about 100 percent and desirably no more than about 50 percent before being attached to the absorbent article. In such a configuration, the side zones 64 and 66 of the waist flap 60 are capable of elongating at least about 25 percent and desirably at least about 50 percent more than the rear waist elastic 46 before they are attached.

As representatively illustrated in FIGS. 1–4, the diaper 10 of the present invention also includes fastening means, such as adhesive tapes 50, to secure the diaper article on a wearer. In a particular embodiment, it is desirable that the fastening means be attached to the waist flap 60 adjacent the side edges 19 of the diaper 10. In such a configuration, the waist flap 60 is placed under direct tension when the side edges of the diaper article are laterally extended to fasten the article about the wearer. Applicant has discovered that such a location of the fastening means along with the stretchable side zones 64 and 66 of the waist flap 60 ensures that the waist flap 60 is correctly positioned such that the pocket 68 remains open to receive body exudates in use. The location of the fastening means on the waist flap 60 also ensures that the side zones 64 and 66 are correctly positioned on the convex surface of the hips of the wearer to maintain the diaper on the wearer in the correct position in use.

Figure 5:
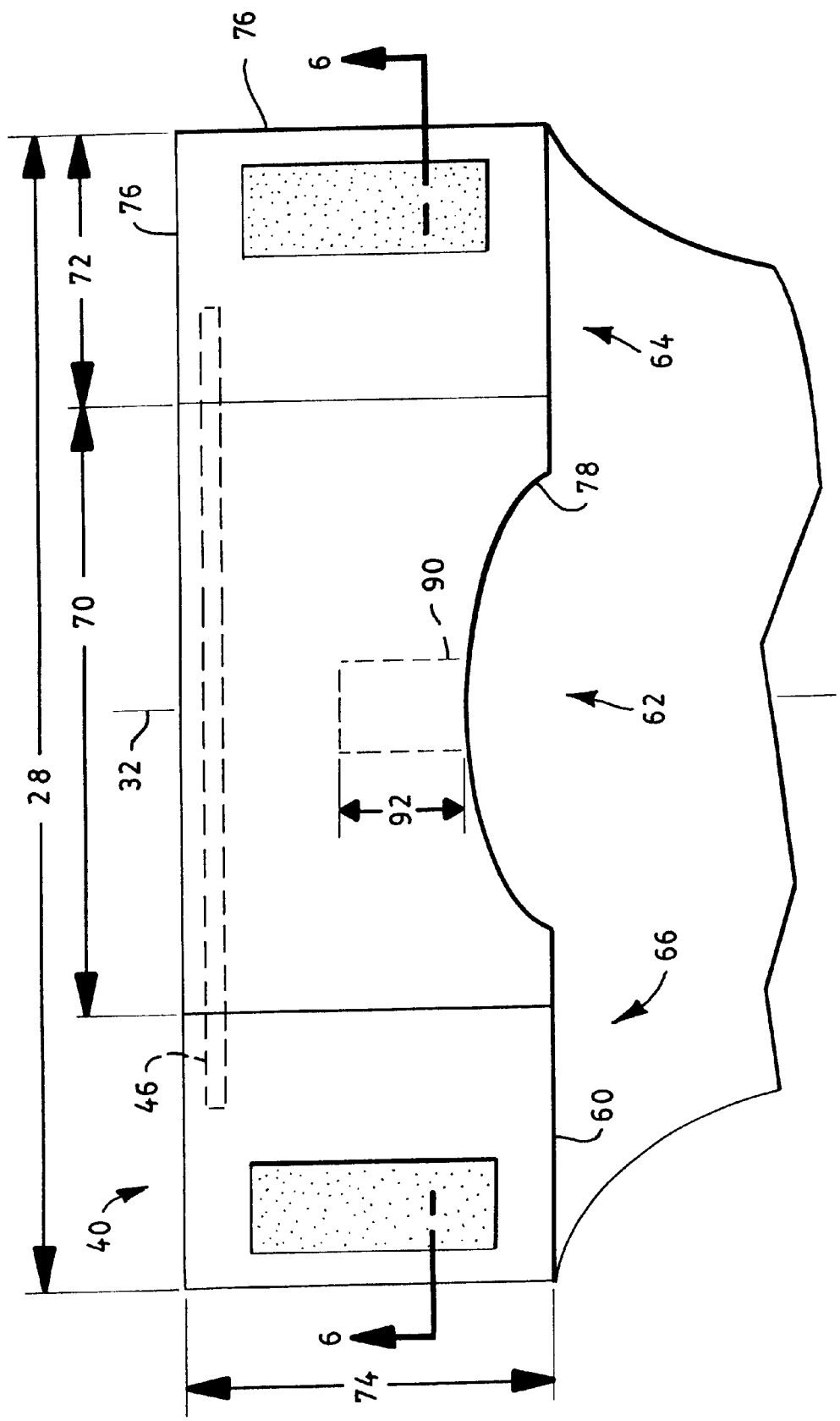
FIG. 5 representatively shows a partially cut away, top plan view of a back waist flap of an absorbent article according to another embodiment of the invention.
Figure 6:
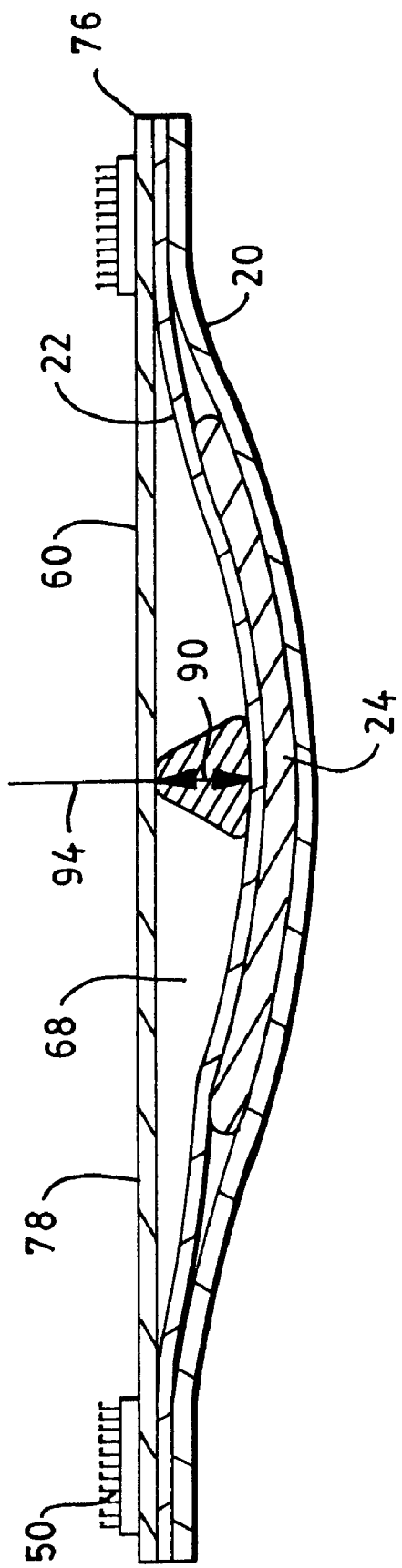
FIG. 6 representatively shows a sectional view of the absorbent article of FIG. 5 taken along line 6—6.

FIGS. 5 and 6 representatively illustrate an alternative embodiment of the waist flap 60 of the invention wherein like numerals represent like elements. As representatively illustrated, the waist flap 60 of the diaper 10 may further include a spacer 90 which may be located between the waist flap 60 and the topsheet 22 of the diaper 10 to maintain the free edge 78 of the waist flap 60 in a spaced apart relationship from the topsheet 22. Thus, the spacer 90 is configured to maintain the pocket 68 between the topsheet 22 and the waist flap 60 in a open configuration to receive and contain body exudates. The spacer 90 may be located in any position which provides the desired spaced apart relationship. Generally, the spacer 90 is located along the central zone 62 of the waist flap 60. In such a configuration, the spacer 90 has been found to provide improved performance when the central zone 62 of the waist flap 60 is substantially incapable of being elongated in the lateral direction 30 from a relaxed condition. This allows the spacer 90 to function to space the waist flap 60 from the topsheet 22 and press the bodyfacing surface of the central zone 62 of the waist flap 60 into a sealing relationship with the wearers body.

The majority of leaks which occur along the rear waist section 14 of the diaper 10 have been found to be caused by the longitudinal flow of body exudates along the gluteal fold region between the buttocks of the wearers body. As a result, the use of the spacer 90 of the present invention is particularly desirable when the waist flap 60 is disposed in the rear waist section 14 of the diaper 10. In such an arrangement, the spacer 90 may be further configured to press the rear waist flap 60 into a sealing relationship with the gluteal fold on the wearers body. For example, the spacer 90 may extend along the longitudinal centerline 32 of the diaper 10 between the topsheet 22 and the waist flap 60 to press the bodyfacing surface of the waist flap 90 into the wearer's gluteal fold region. In a particular embodiment, the spacer 90 extends longitudinally from a point inwardly behind the free edge 78 of the rear waist flap 60 outward towards the respective end edge 18 of the diaper 10 in the rear waist section 14. In such a configuration, the spacer 90 not only functions to better maintain the pocket 68 in an open configuration to contain the body exudates but may also function as a block or dam to the longitudinal flow of body exudates along the gluteal fold of the wearer for improved overall performance.

Alternatively, the spacer 90 may define a conduit therein which is capable of receiving body exudates and transporting the exudates into the rear waist section of the article between the waist flap 60 and the topsheet of the article. For example, the spacer may be a tube having an inside diameter of from about 0.25 to about 5 centimeters.

The spacer 90 may have any shape and size which provides the desired spaced apart relationship between the topsheet 22 and the waist flap 60. As representatively illustrated in FIGS. 5 and 6, the spacer 90 defines a longitudinally extending structure having a length 92 and a height 94. Desirably, the spacer 90 defines a length of from about 0.5 to about 5 centimeters, and more desirably from about 1 to about 3 centimeters such that it has a sufficient amount of surface contacting the waist flap 60 to maintain the spaced apart relationship. In addition, it is desirable that the spacer 90 define a height of at least about 0.25, more desirably at least about 0.5, and even more desirably at least about 1.0 centimeters to maintain the pocket open to receive body exudates. The spacer 90 may have a circular, triangular, square, rectangular, diamond, or the like cross sectional shape which may or may not have a hole therethrough. In a particular embodiment, the spacer 90 has a solid triangular cross section to press the bodyfacing surface of the waist flap 60 into the gluteal fold of the wearer's body to effectively seal and block the longitudinal flow of body exudates along the gluteal fold.

The spacer 90 may be made from a variety of suitable materials which are resilient to allow some compression and being able to curve and bend without allowing enough deformation such that the pocket 68 becomes to small, or collapsed. The resiliency of the spacer 90 ensures that it does not cause excessive redmarking on the wearer's body while maintaining the void volume in the pocket 68 between the waist flap 60 and the topsheet 22 of the diaper 10. For example, suitable materials for the spacer 90 include clay materials, foam materials, and the like, or composite materials such as a core of cellulosic material such as that used in the absorbent body 24 which has been enclosed within a nonwoven or film layer.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

I claim:

1. An absorbent article having an absorbent body, a longitudinal centerline, a lateral centerline, a front waist section, a rear waist section, an intermediate section which interconnects said front and rear waist sections, a pair of longitudinally opposed end edges in respective front and rear waist sections, and a pair of laterally opposed side edges, said absorbent article further comprising a waist flap which is attached adjacent one of said longitudinally opposed end edges of said absorbent article in one of said front and said rear waist sections and which extends inwardly towards said intermediate section to create a pocket between said waist flap and said waist section wherein said waist flap defines a central zone and a pair of laterally opposed side zones which are connected to and extend outwardly in a lateral direction from said central zone to said side edges of said absorbent article and wherein each of said side zones is configured to elongate in said lateral direction at least about 25 percent more than said central zone when said side edges of said absorbent article are extended outwardly in said lateral direction.

2. An absorbent article according to claim 1 wherein said central zone of said waist flap is centered about said longitudinal centerline of said absorbent article and defines a width which is at least about 10 percent of a width of said absorbent article in said one of said waist sections.

3. An absorbent article according to claim 2 wherein said width of said central zone of said waist flap is at least about 20 percent of said width of said absorbent article.

4. An absorbent article according to claim 1 wherein each of said side zones of said waist flap is capable of being elongated in said lateral direction at least about 50 percent from a relaxed condition.

5. An absorbent article according to claim 1 wherein said central zone of said waist flap is capable of being elongated in said lateral direction no more than about 50 percent from a relaxed condition and each of said side zones of said waist flap is capable of being elongated in said lateral direction at least about 100 percent from a relaxed condition.

6. An absorbent article according to claim 1 wherein each of said side zones is configured to elongate in said lateral direction at least about 50 percent more than said central zone when said side edges of said absorbent article are extended outwardly in said lateral direction.

\* \* \* \* \*